United States Patent [19]
Kisima et al.

[11] Patent Number: 4,995,273
[45] Date of Patent: Feb. 26, 1991

[54] METHOD OF AN APPARATUS FOR WEATHER RESISTANCE TEST

[75] Inventors: Yoshio Kisima, Tokyo; Teruo Iwanaga; Hitoshi Goto, both of Gyoda, all of Japan

[73] Assignee: Dainippon Plastics Co., Ltd., Tokyo, Japan

[21] Appl. No.: 353,727

[22] Filed: May 18, 1989

[30] Foreign Application Priority Data

May 31, 1988 [JP] Japan .................. 63-131627

[51] Int. Cl.$^5$ ............................ G01N 17/00
[52] U.S. Cl. ..................... 73/865.6; 73/73; 374/57
[58] Field of Search ............... 374/7, 28, 57; 73/865.6, 150 R

[56] References Cited

U.S. PATENT DOCUMENTS

| | | | |
|---|---|---|---|
| 1,827,530 | 10/1931 | LeGrand | 73/865.6 X |
| 2,904,995 | 9/1959 | Obermaier | 374/28 |
| 3,488,681 | 1/1970 | Mita et al. | 73/865.6 X |
| 4,012,954 | 3/1977 | Klippert | 73/865.6 X |
| 4,698,507 | 10/1987 | Tator et al. | 250/429 |
| 4,817,447 | 4/1989 | Kashima et al. | 374/57 X |

FOREIGN PATENT DOCUMENTS

| | | |
|---|---|---|
| 55-13541 | 4/1980 | Japan . |
| 58-90146 | 5/1983 | Japan . |
| 60-117128 | 6/1985 | Japan . |
| 60-117129 | 6/1985 | Japan . |
| 62-29744 | 12/1987 | Japan . |

OTHER PUBLICATIONS

Japanese Industrial Standard (JIS), "Glass enclosed Carbon-Arc Type Apparatus for Artificial Light Exposure Tests", JIS B 7751-1974.
Japanese Industrial Standard (JIS), "Light-and-Water-Exposure Apparatus (Enclosed Carbon-Arc Type)", JIS B 7752-1980.
Japanese Industrial Standard (JIS), "Light-and Water-Exposure Apparatus (Open-Flame Sunshine Carbon-Arc Type)", JIS B 7753-1988.
Japanese Industrial Standard (JIS), "Light-Exposure and Light-and-Water-Exposure Apparatus (Xenon-Arc Lamp Type)", JIS B 7754-1979.

Primary Examiner—Daniel M. Yasich
Attorney, Agent, or Firm—Armstrong, Nikaido, Marmelstein, Kubovcik & Murray

[57] ABSTRACT

A method of and apparatus for weather resistance test comprising a process for washing the surface of samples with a cleaner which is added at least between a process for condensing moisture on the surface of the sample after ultraviolet radiation has been applied and the process for again applying ultraviolet radiation after the process for condensing moisture. Impurities adhered to the surface of the sample and substances extracted on the surface of the sample can be removed by washing with the cleaner so that the surface of the sample to which these impurities and substances are adhered intact can be protected from being baked in the ensuing ultraviolet radiation application process. Consequently, generation of spot patterns and excessive color change of the surface of the sample can be prevented.

18 Claims, 12 Drawing Sheets

METHOD OF AN APPARATUS FOR WEATHER RESISTANCE TEST

BACKGROUND OF THE INVENTION

Field of the Invention

The present invention relates to a method of and apparatus for weather resistance test, and, more particularly to a method of and an apparatus for a weather resistance test of plastics, paint, ink, pigment, fiber with which the results obtained can satisfactorily simulate the outdoor natural deterioration.

Hitherto, when it is intended to test the weather resistance of plastics and paint or the like, a weather meter in accordance with any of JIS (Japanese Industrial Standards) B7751 to 7754 is generally used. Each of the weather meters of the types described above comprise a light sources such as a carbon arc lamp or a xenon arc lamp as to have the beams from this light source applied to the samples As a result, this allows an accelerated weathering test to be carried out.

However, the intensity of the ultraviolet rays radiated from the light source of the above-described type weather meter to be applied to the samples is, in general, limited to an unsatisfactory level of substantially 6 mW per 1 cm$^2$ of the surface of the sample to be tested. Therefore, it takes several hundred hours or longer to measure or evaluate the characteristics of the ultraviolet ray deterioration which will occur to equate with the deterioration caused by the sun's rays in one year.

Furthermore, a method in which all of the samples in each of the lots are subjected to the test has been so far employed in general. Therefore, it takes an excessively long time to complete the test and to evaluate the results, causing a problem in terms of efficiency.

To this end, in order to overcome the above-described problems, the inventors of the present invention disclosed the following weather meter in Japanese Patent Laid-Open Nos. 60-117128 and 60-117129, that is, a weather meter serving as a pre-weather meter for performing a pre-weather resistance test was disclosed, which allows ultraviolet ray deterioration to be evaluated in a significantly shortened time, for example, in one tenth or less of the time taken in a conventional test period of time and which involves means for applying intense ultraviolet rays of substantially 50 mW or more per 1 cm$^2$ of the surface of the sample to be tested by using a metal halide lamp beam applied to the samples of each of the lots before having the samples subjected to the weather meter.

It is preferable for the weather resistance test to be conducted under the physical conditions similar to the actual conditions with which the samples such as plastics or paint are subjected. In particular at night, not only the sample is subjected to a state in which no sun rays are applied and of low temperatures but also it can be readily subjected to a dew or moisture condensed state due to the low temperatures at night.

Therefore, it is preferable for the weather resistance test or its pre-test to be made under such dew condensation conditions in order to obtain test results which can simulate the natural outdoor deterioration.

Hitherto, as a method to make such dew condensation conditions for samples, a method was disclosed in Japanese Patent Publication No. 55-13541 in which samples are watered. However, such watering method cannot faithfully simulate actual dew condensation conditions and this is unsatisfactory.

The inventors of the present invention have conceived a method of providing an actual dew condensation state for samples by adjusting the temperature of the sample and both the temperature and the humidity of the ambient air surrounding it. Then the inventors have disclosed the following weather meter in Japanese Patent Laid-Open No. 62-297744. This weather meter is arranged in such a manner that temperature adjusting means is provided for a sample holder and a humidifier is disposed in a chamber of the region in which the thus-provided sample holder is disposed, and by making specific working conditions through control means, the temperature of the sample is lowered below its dew point during an interruption of radiation from the ultraviolet ray source, causing the sample to be brought to a dew condensed state which approximates natural dew condensation.

As means to form dew condensation on the surface of the sample, a method of spraying cooling water to the reverse side of the sample was disclosed, and another method is also disclosed in Japanese Patent Laid-Open No. 58-90146 in which the sample is cooled down by means of a thermoelectric cooling element.

The inventors have found a fact that spot patterns appear on the surface of the sample and the color of the surface of the sample considerably changes in accordance with time lapse as shown in FIGS. 10A and 10B of a microphotograph of the surface of the sample when the above-described dew condensation process is added to the accelerated weathering test in which ultraviolet rays are applied to the sample, where FIG. 10A is a metallurgical microphotograph, enlarged by 200 times, of the surface of the sample which has not been subjected to the test as yet, while FIG. 10B is the same enlarged by 200 times, of the surface of the sample which has been subjected to the weather resistance test for 50 hours. In addition, a fact has been found that the above-described phenomenon particularly appears significantly when this dew condensation process is added to the above-described accelerated weathering test in which the intensity of the ultraviolet rays to be applied is strong.

Such a spot pattern or significant color change do not appear in the case where the sample is placed outdoor naturally. Therefore, this phenomenon presents a serious problem in making the simulation between the natural deterioration and the results of the weather resistance test.

Such spot patterns can be caused from the following reason: impurities contained in the condensed dew appeared on the surface of the sample during the dew condensation process or substances extracted from the sample due to the dew condensation are adhered to the surface of the sample; and then the extraneous matter on the surface of the sample is baked on this surface of the sample due to the lens effect of the residual condensed dew during the application of the ultraviolet rays performed after the dew condensation process; as a result, the above-described spot pattern can be generated.

In order to prevent the spot pattern, it might be considered feasible to employ a method in which the sample is slanted or stood erect for the purpose of having the residual dew on the surface of the sample allowed to fall, another method in which air is blown for the purpose of blowing off the dew, and a still further method in which the residual dew on the surface of the sample is dried up as to be readily removed. However, any of these methods can not achieve a satisfactory effect.

SUMMARY OF THE INVENTION

To this end, an object of the present invention is to provide a method of and an apparatus for a weather resistance test capable of overcoming the above-described problems experienced with the previously disclosed weather resistance tests in which the dew condensation process is added, whereby any spot pattern or color change cannot be generated, and a satisfactory test results which satisfactorily simulates the outdoor natural deterioration results can be obtained even if the dew condensation process is added to the weather resistance test.

A method of weather resistance tests according to the present invention includes a process for applying to a sample ultraviolet rays from an artificial light source, a process for condensing dew on the surface of this sample, and a process for again applying ultraviolet rays to the above-described sample after the process for condensing dew, the method comprising:

a process for washing the surface of the sample with a cleaner which is added at least between the process for condensing the dew on the surface of the sample after the process for applying ultraviolet rays and the process for again applying ultraviolet rays after the process for condensing dew.

As described above, impurities adhered to the surface of the sample or substances extracted on the surface of the sample during the dew condensation process can be washed and removed by the cleaner since the process for washing the surface of the sample with a cleaner is added at least between the process for condensing dew on the surface of the sample after the process for applying ultraviolet rays and the process for again applying the ultraviolet rays after the process for condensing dew. Therefore, these substances cannot be baked on the surface of the sample in the ensuing process for applying ultraviolet rays and be adhered intact to the same. As a result, generation of the spot pattern on the surface of the sample can be effectively prevented, and thereby the excessive color change on the surface of the sample can be prevented.

An apparatus for weather resistance tests according to the present invention comprises means for holding a sample, means for applying ultraviolet rays to the sample surface, means for condensing dew on the surface of the sample, means for washing the surface of the sample with a cleaner, and means for controlling the operation of each of the above-described means.

As described above, generation of the spot pattern and significant color change of the surface of the sample can be effectively prevented by a simple structure apparatus for which only means for washing the surface of the sample with a cleaner is additionally provided. Consequently, test results which satisfactorily simulate the natural deterioration can be readily obtained.

BRIEF DESCRIPTION OF THE DRAWINGS

FIG. 10A is a metallurgical microphotograph 200 times enlarged) of the surface of the sample before start of the test; and FIGS. 10B, 10C, and 10D are metallurgical microphotograph (200 times enlarged) which illustrates the state of deterioration of the surface of the sample due to each of the tests according to the conventional example, and according to the present invention, and the outdoor exposure test.

DESCRIPTION OF THE PREFERRED EMBODIMENT

Figure 1:
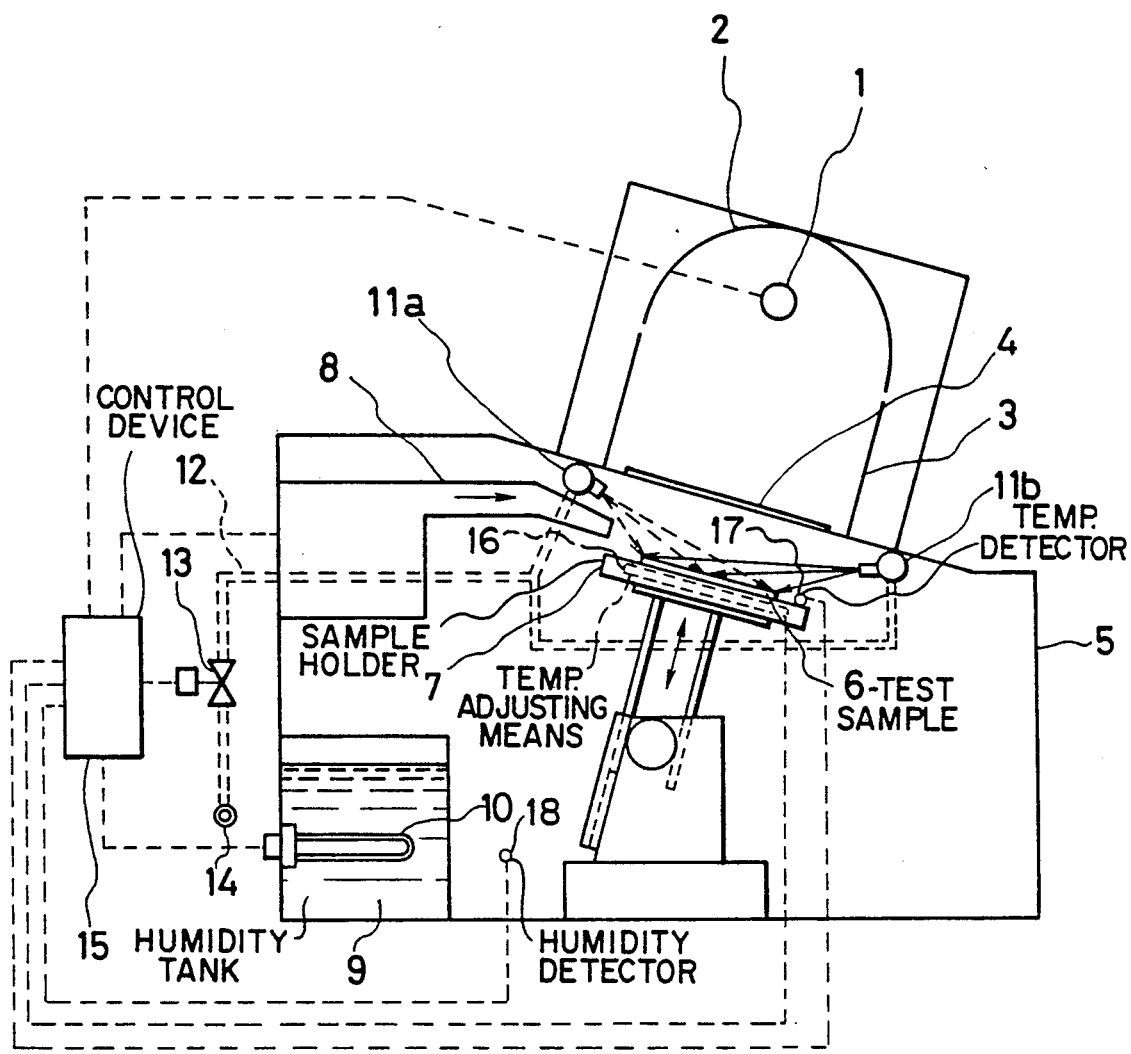
FIG. 1 is a schematic view of an embodiment of an apparatus for weather resistance test according to the present invention.

An embodiment of the present invention will now be described. FIG. 1 is a schematic view which illustrates an embodiment of an apparatus for weather resistance test according to the present invention, where reference numeral 1 represents a light source comprising a metal halide lamp displaying considerably great energy in the wavelength region for example, from 300 to 450 nm, a filter for restricting the wavelength region to 300 to 450 nm, a water cooling jacket, and so on. This light source 1 is accommodated in a reflecting plate comprising a doom-shaped main reflecting plate 2 for producing parallel beams and a sub-reflecting plate 3 for parallel beams. Reference numeral 4 represents a shield plate made of quarts glass through which ultraviolet rays can transmit and capable of separating the sample chamber 5 from the light source portion.

Reference numeral 7 represents a sample holder disposed in the sample chamber 5 to which a sample 6 is attached, and a temperature adjusting means such as a water cooling means or thermoelectric cooling means is as well provided for this sample holder 7. Reference numeral 8 represents an air blowing nozzle for maintaining the temperature of the sample at a predetermined degree by blowing air of a predetermined temperature to the sample 6 attached to the sample holder 7. Reference numeral 9 represents a humidifying tank for humidifying the sample chamber 5 in which heater 10 for heating the humidifying tank 9 is provided. Reference numerals 11a and 11b represent spray nozzles for spraying cleaner to the sample 6 attached to the sample holder 7. As this cleaner, water, a surface active agent, water containing air, alcohol or the like can be employed.

The sample holder 7 is disposed such that the same is inclined by, for example, 15 for the purpose of preventing stagnancy of sprayed cleaner and of making the sprayed cleaner flow downwards. Also the light source 1 is inclined and is attached to the sample chamber 5. The sample chamber 5 is further provided with a temperature detector 17 and humidity detector 18. Referring to this drawing, reference numeral 12 represents pipes arranged to be connected to the spray nozzle 11a and 11b, 13 represents an electromagnetic valve for controlling the cleaner supply, 14 represents a cleaner supply port, 15 represents a control device for controlling the light source 1, the air blowing nozzle 8, heater 10 in the humidifying tank 9, the electromagnetic value 13, the temperature adjusting means provided for the sample holder 7 in accordance with a predetermined process.

In the thus-structured apparatus for weather resistance tests, the sample 6 placed on the sample holder 7 is first applied with ultraviolet rays for a predetermined time, for example, for 4 hours, when the light source 1 is turned on. In this case, the temperature of the sample 6 is maintained at a predetermined degree (40° to 100° C.±1.0° C.) by air injected by the blowing nozzle 8 in response to a detection signal supplied from the temperature detector 17. When the application of ultraviolet rays is stopped as a result of the turning off action of the light source 1, the temperature of the sample holder 7 is lowered below its dew point in response to the detection signal supplied from the temperature detector by the temperature adjusting means 16 provided for the sample holder 7. Furthermore, steam is generated by heating the humidifying tank 9 as to humidify the sample chamber 5 at a predetermined humidity as determined by humidity detector 18. As a result, dew condenses on the surface of the sample 6 held by the sample holder 7.

After the continuation of this dew condensation state for a predetermined period of time, for example, substantially one hour, the electromagnetic valve 13 is actuated by a control signal supplied from the control device 15, and the spray nozzles 11a and 11b are operated as to inject the cleaner to the sample 6. As a result, dew condensed on the surface of the sample is removed and this sample itself is washed. Next, the light source 1 is again turned on so that ultraviolet rays are applied to the sample 6. Then, the above-described process is repeated.

By conducting the weather resistance test in the manner as described above, the conditions which significantly simulate the dew condensation state at night in the outdoor exposure state can be made for the sample. In addition, the generation of the spot pattern on the surface of the sample and the excessive change in color of the surface of the sample can be prevented. As a result, the results of weather resistance tests which can significantly simulate the natural deterioration can be obtained in a significantly short time period.

In the above-described embodiment, although the washing process is added between the dew condensation process and the ensuing ultraviolet rays application process, it may be further added after the application of ultraviolet rays but before the ensuing next dew condensation process. In this case, a further significant effect to prevent generation of the sport pattern and the significant color change can be obtained. In addition, this washing process may be effectively added in the dew condensation process.

In the above-described embodiment, although two spray nozzles for injecting the cleaner are provided on the right and left sides above the sample, the number and the positions of the spray nozzles are not limited to this description. They may be optionally determined on the basis of the shape, size or the like of the sample holder.

As the means for cleaning the sample, a means arranged to spray the surface of the sample with hot steam can be employed. Alternatively, an ultrasonic washer may also be used.

Then, the results of the tests conducted simultaneously with the weather resistance tests according to the conventional test method will be described for the purpose of confirming the effects of the method of weather resistance tests according to the present invention.

(1) Test conditions according to the present invention
light source used: metal halide lamp 4 kW
irradiation wavelength: 300 to 450 nm
temperature of the black panel (when ultraviolet rays are applied): 63° C.±3° C.
intensity of ultraviolet rays on the surface of the sample: 100 ±5 mW/cm$^2$
humidity at the sample chamber at the time of dew condensation: 95% or higher
temperature of the sample at the time of dew condensation: 30° C.
application of ultraviolet rays and dew condensation cycle: ultraviolet rays are applied for 4 hours, dew condensation for 1 hour
washing period: 30 seconds after the application of ultraviolet rays and 30 seconds after the dew condensation
cleaner: ion exchange water
temperature of the cleaner: 20° C.
quantity of the cleaner to be sprayed: 9 cc per 1 cm$^2$ of the surface of the sample
pressure of the cleaner injected: 1.5 kg/cm$^2$ (2) Test conditions for conventional example 1 (sunshine weather-meter)
light source used: sunshine carbon arc lamp
irradiation wavelength: 280 to 1400 nm
temperature of the black panel: 63°±3° C.
intensity of ultraviolet rays at the surface of the sample: 5 mW/cm$^2$ (3) Test conditions for conventional example 2 (xenon weather-meter)
light source used: xenon arc lamp 3.5 kW
irradiation wavelength: 300 to 1400 nm
temperature of the black panel: 63°±3° C.
intensity of ultraviolet rays on the surface of the sample: 2.3 mW/cm$^2$ (4) Test conditions for conventional example 3 (only dew condensation process is added, but no washing process is added)
light source used, application of ultraviolet rays and the dew condensation cycle are the same as those for the test according to the present invention (5) Test conditions for referential example 1 (outdoor exposure)
time period: 12 months from May 1987 to April 1988 location: Matsudo city, Chiba prefecture, Japan (6) Test conditions for referential example 2 (a process for water is added after the ultraviolet ray application process)
light source used: metal halide lamp 4 kW
irradiation wavelength: 300 to 450 nm
temperature of the black panel: 63° C.±3° C.
intensity of ultraviolet rays on the surface of the sample: 100 ±5 mW/cm$^2$
temperature of the liquid in which the sample is dipped: 24° C.
application of ultraviolet rays and dipping cycle: application for 4 hours, dipping for 1 hour As the sample, hard vinyl chloride prepared under the following conditions was used.

Conditions for preparing the sample
(a) Composition (unit: PHR)
PVC (degree of polymerization=1100): 100
tribase: 1.0
lead stearate: 1.5
dibasic lead stearate: 0.3
calcium stearate: 0.3
calcium carbonate: 8.75
titanium oxide: 0.2
carbon black: 1.0

(b) Molding conditions

Powder mixed in accordance with the above-described composition manner was kneaded in a heat roll at 160° to 170° C. for 5 minutes. The thus obtained raw sheet was pressed at 190° to 195° C. for 10 minutes. After the thus-obtained pressed sheet had been cooled down, the same was made a substantially 1.0 mm sheet serving as a sample.

The thus-prepared sample was subjected to each of the tests under the above-described test conditions so that results of the following factor were tested: 60°- gloss retention rate (this is a factor for measuring change in the reflectance of the the surface of the sample); value L* (this is a factor for measuring change in the lightness of the surface of the sample), value b* (this is a factor for measuring change in the chromaticity in the direction from yellow to blue on the surface of the sample), color difference ΔE* (this is a factor for measuring change in the hue on the surface of the sample) in accordance with CIE1976L*, a*, b* space colorimetric system. The thus-obtained results are shown in FIGS. 2 to 9, and states of generation of spot patterns on the surface of the sample are shown by microphotographs in FIGS. 10A to 10D.

Figure 2:
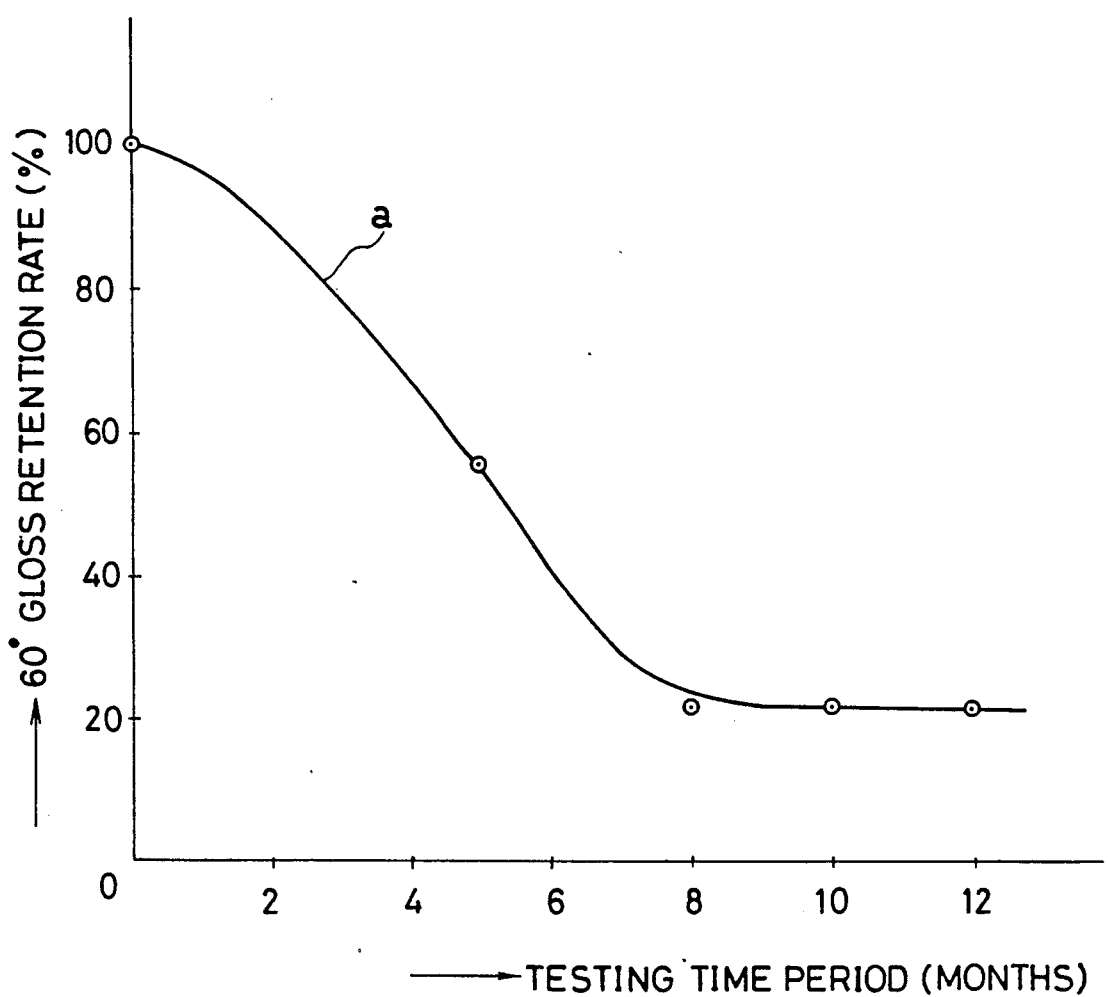
FIG. 2 is a graph which illustrates change in the gloss retention rate in an outdoor exposure test.
Figure 3:
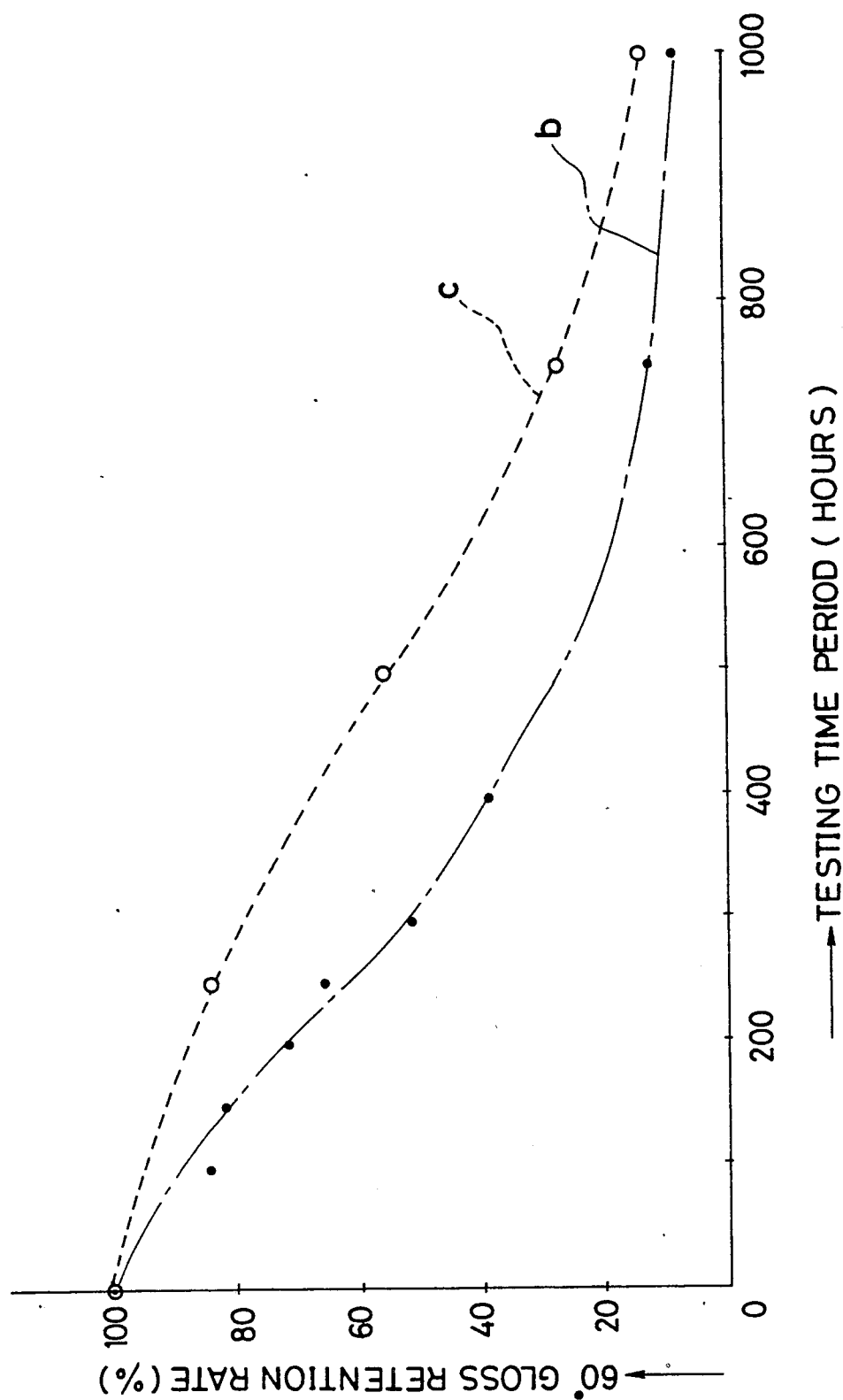
FIG. 3 is a graph which illustrates changes in the gloss retention rates in the test of conventional examples 1 and 2.

Curve a shown in FIG. 2 illustrates change in the gloss retention rate in the outdoor exposure test. As is shown, it is rapidly lowered to 20% in 8 months from the start of the test, while it does not display any significant change thereafter. On the other hand, with the sunshine weather-meter (conventional example 1) a tendency similar to that of the outdoor exposure test is displayed as designated by curve b shown in FIG. 3. With the xenon weather-meter (conventional example 2), a substantially straight change is displayed as designated by curve c in the same drawing. It is apparent that it takes 600 to 800 hours for both of the above-described tests to have the gloss retention rate lowered to 20%.

Figure 4:
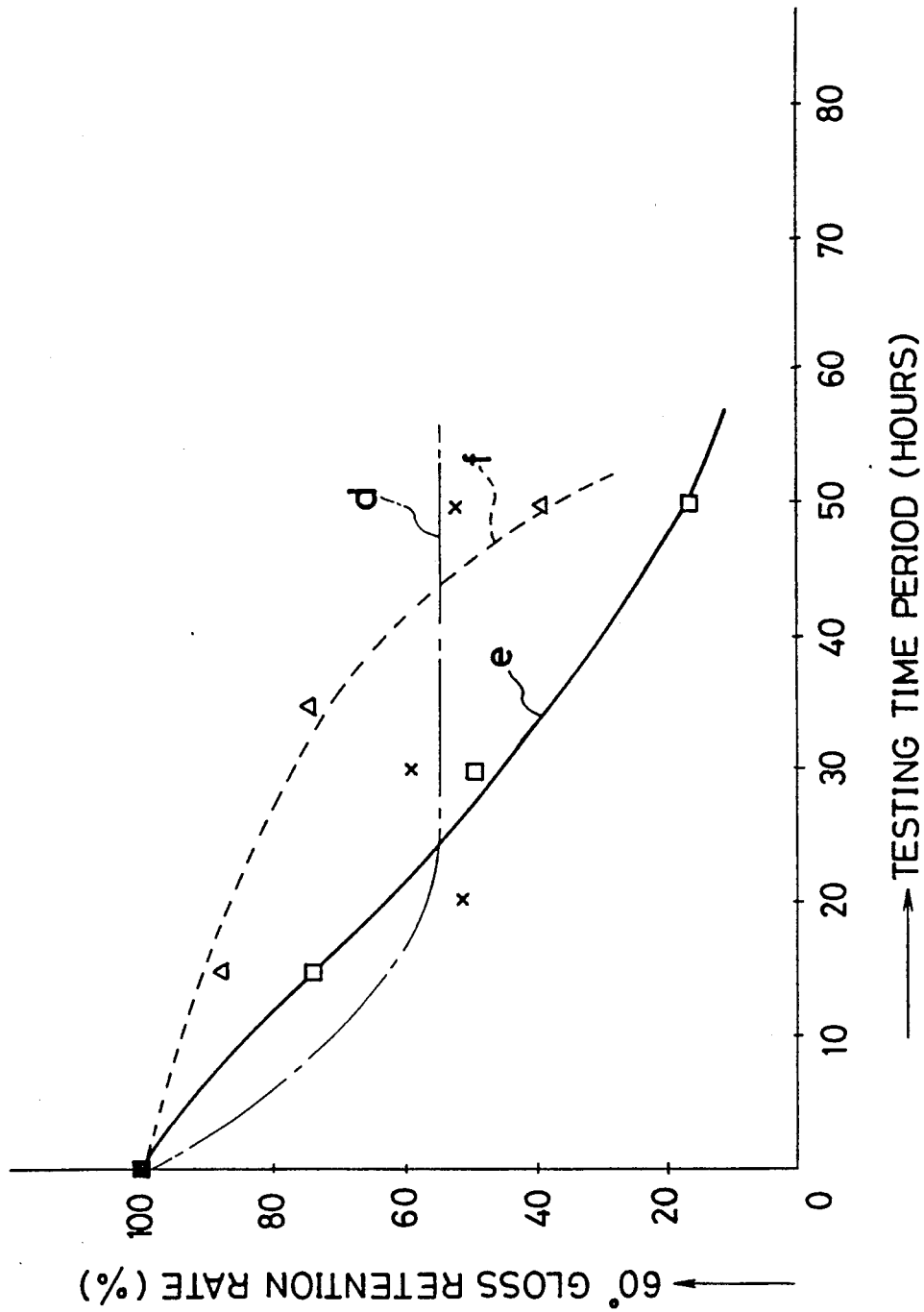
FIG. 4 is a graph which illustrates changes in the gloss retention rates in a test according to the present invention, a conventional example 3, and referential example 2.

To the contrary, in the case of the conventional example 3 in which only the dew condensation process is added, the gloss retention rate does not display any significant change after it has been lowered to 50% in a relatively short time of substantially 20 hours after the start of the test as designated by curve d shown in FIG. 4. However, with the method according to the present invention, the retention rate is lowered to 20% prior to lapse of test time period of 50 hours designated by curve e shown in the same drawing. As is shown, with the method according to the present invention, it takes only substantially one tenth or less of time taken in the conventional examples 1 and 2 for the gloss retention rate of the same to be made the degree of deterioration which simulates the degree of deterioration realized from 8 months of outdoor exposing. In the referential example 2 in which the water dipping process is additionally provided, although the tendency of lowering of the gloss retention rate during the test is different, but a deterioration results similar to the deterioration results realized by the present invention can be obtained as designated by curve f shown in FIG. 4.

Figure 5:
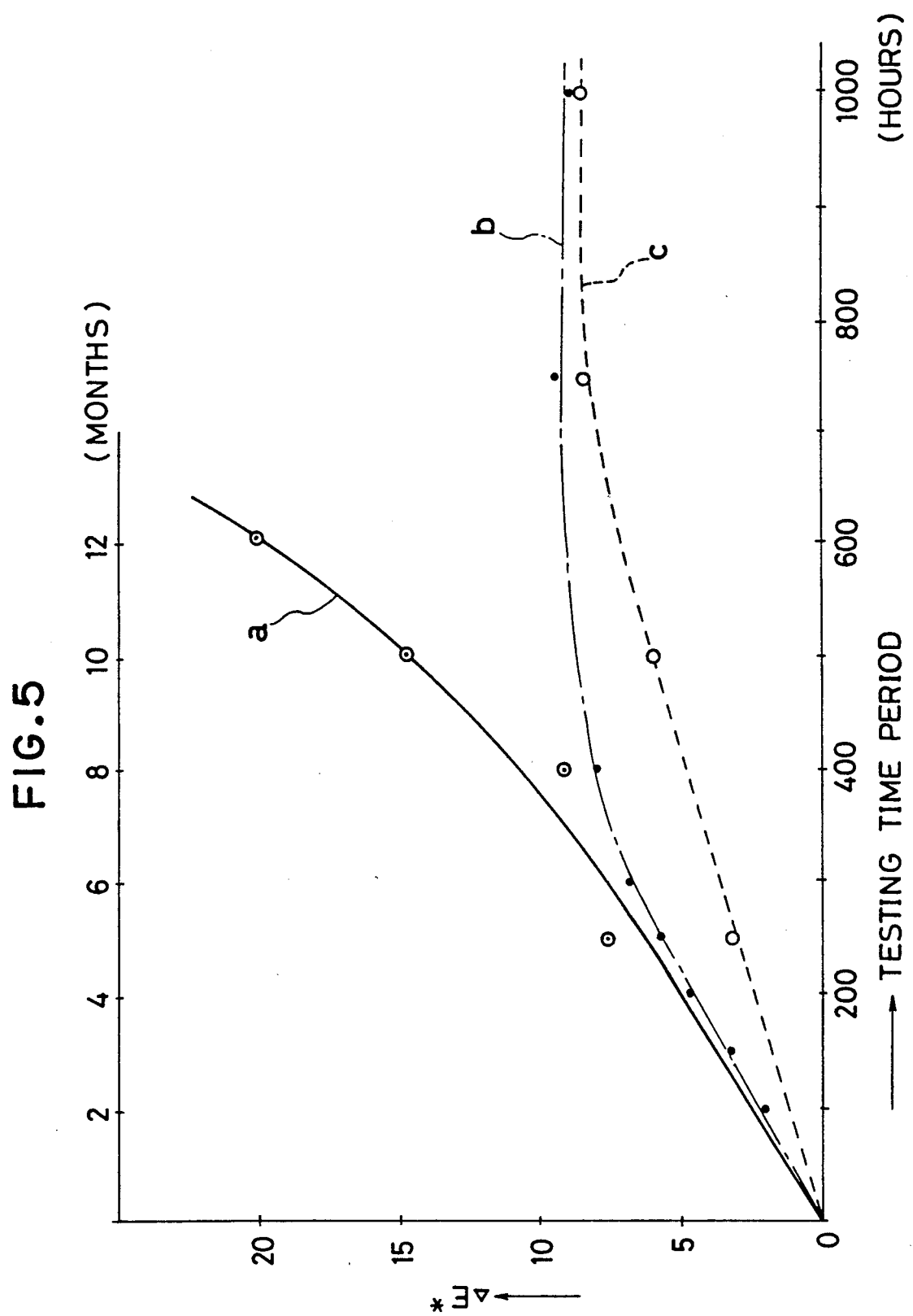
FIG. 5 is a graph which illustrates changes in color difference $\Delta E^*$ in the outdoor exposure test, and in the test according to the conventional examples 1 and 2.

Then, as for color difference ΔE*m, as designated by curve a shown in FIG. 5, it rises substantially linearly in the outdoor exposure case, and value ΔE* reaches 20 after 12 months have been elapsed. Then, it tends to rapidly rise. However, with the conventional examples 1 and 2, even it testing time period reaches 1000 hours, value ΔE* does not reach 10 since a saturated state is realized as designated by curves b and c.

Figure 6:
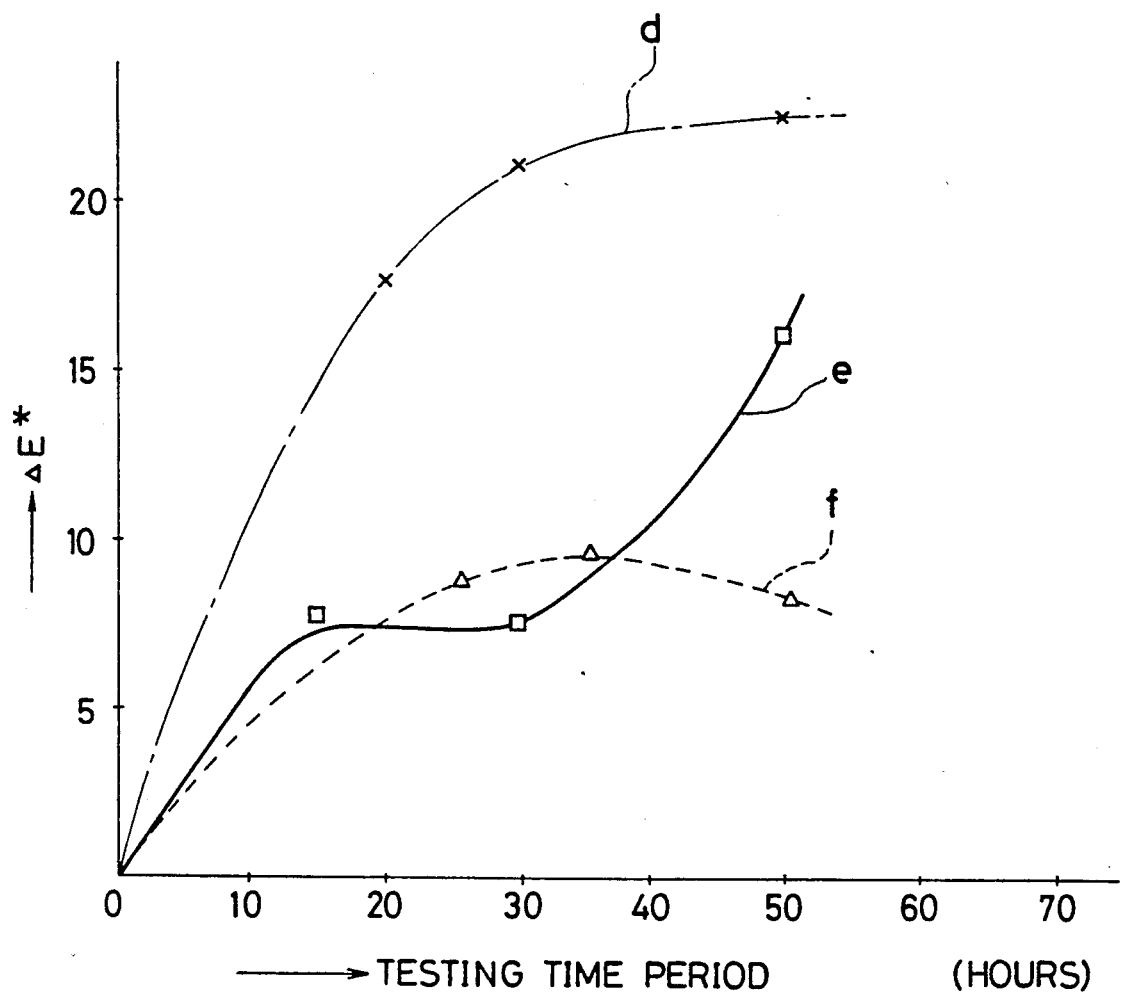
FIG. 6 is a graph which illustrates changes in color difference $\Delta E^*$ in the test according to the present invention, the test according to the conventional example 3 and the referential example 2.

On the other hand, with the conventional example 3, although value ΔE* reaches 20 or more in a relatively short time (substantially 30 hours) as designated by curve d shown in FIG. 6, it is then brought to a saturated state. Value ΔE* according to the present invention reaches, as designated by curve e shown in this drawing, substantially 15 to 50 hours, and then this curve rapidly rise with displaying the similar tendency to the curve according to the outdoor exposure test. As for referential example 2, value ΔE* reaches, as designated by curve f shown in this drawing, substantially 10 at most.

Figure 7A:
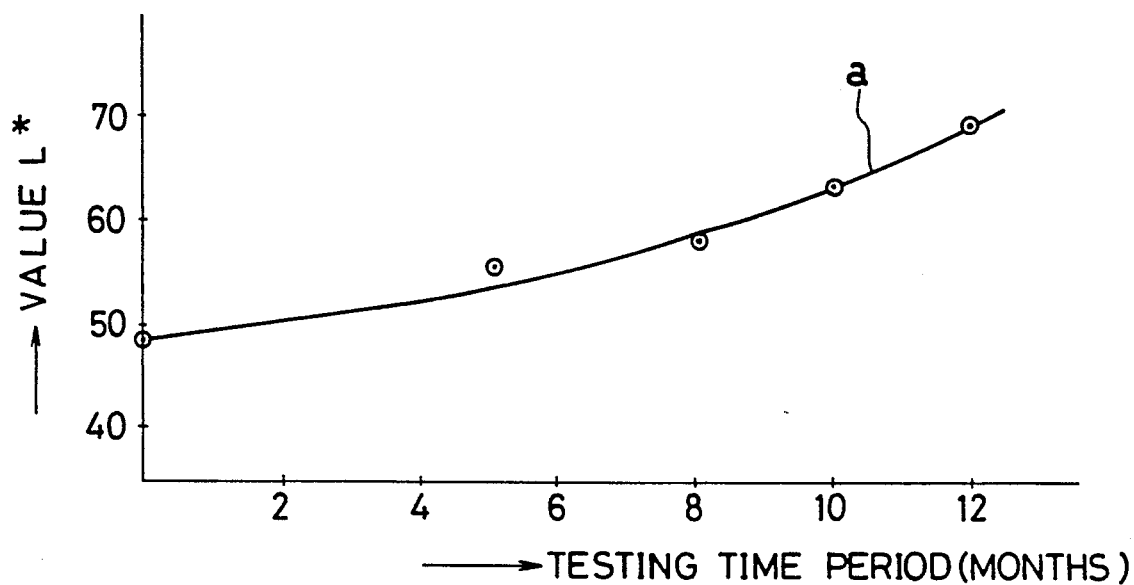
FIG. 7A is a graph which illustrates change in value $L^*$ in the outdoor exposure test.
Figure 7C:
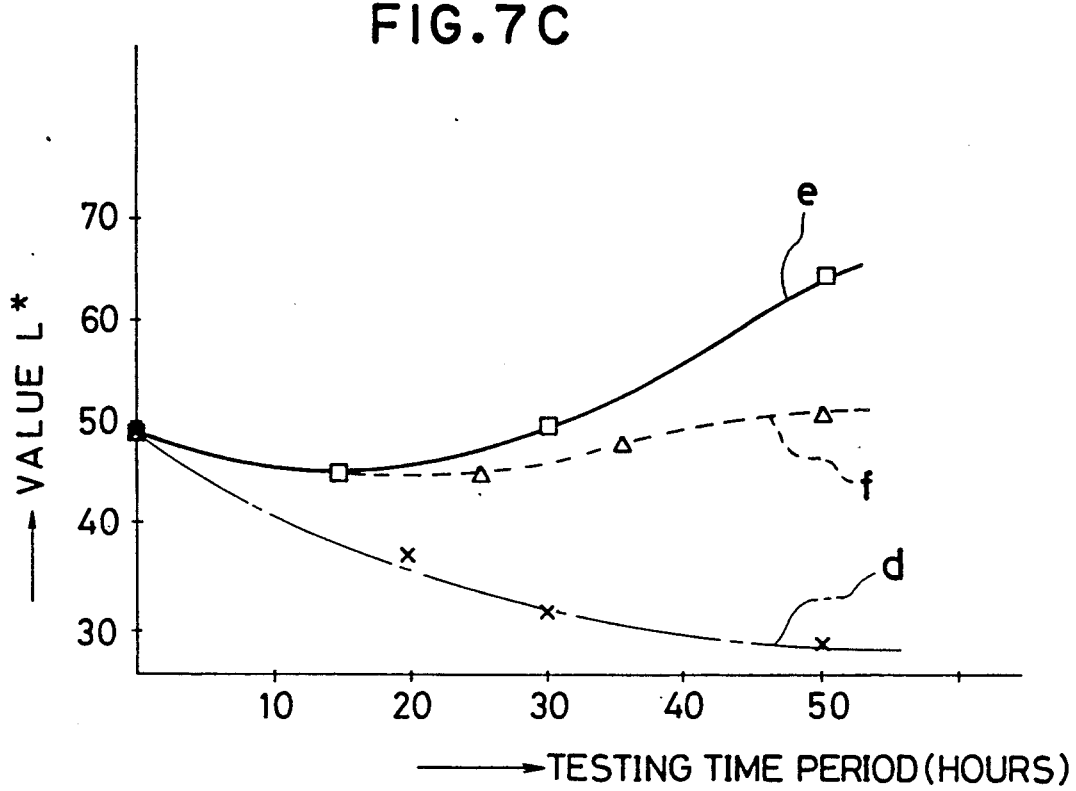
FIG. 7C is a graph which illustrates changes in value $L^*$ in the test according to the present invention and the tests according to the conventional example 3 and referential example 2.
Figure 7B:
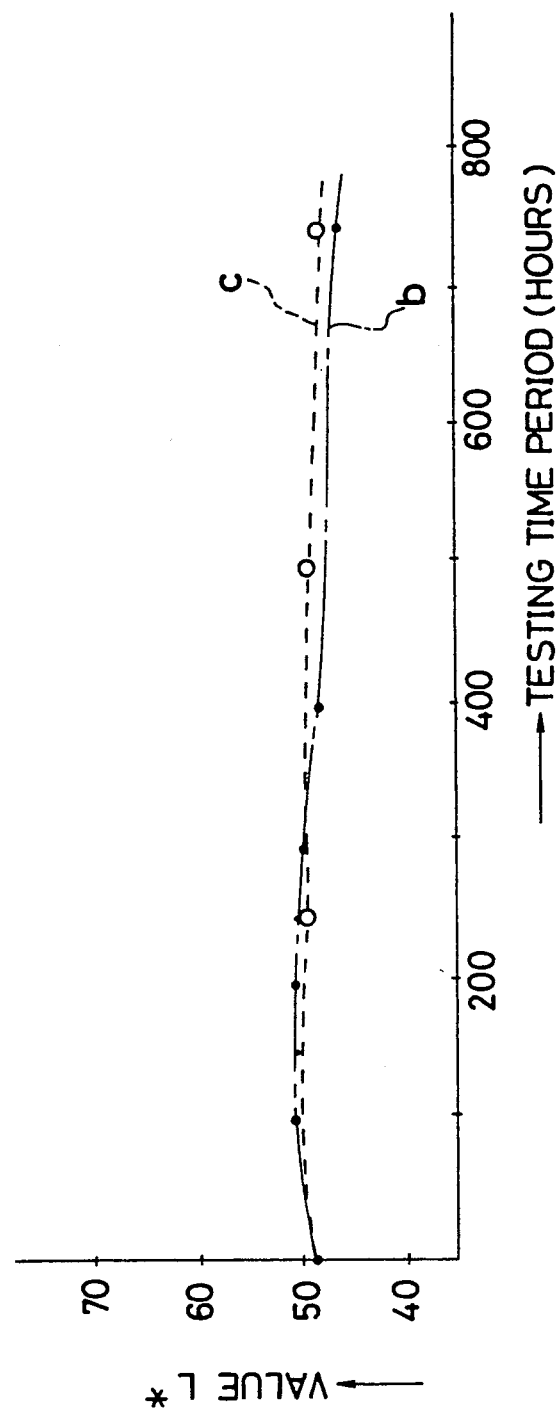
FIG. 7B is a view which illustrates changes in value $L^*$ in the conventional examples 1 and 2.
Figure 8:
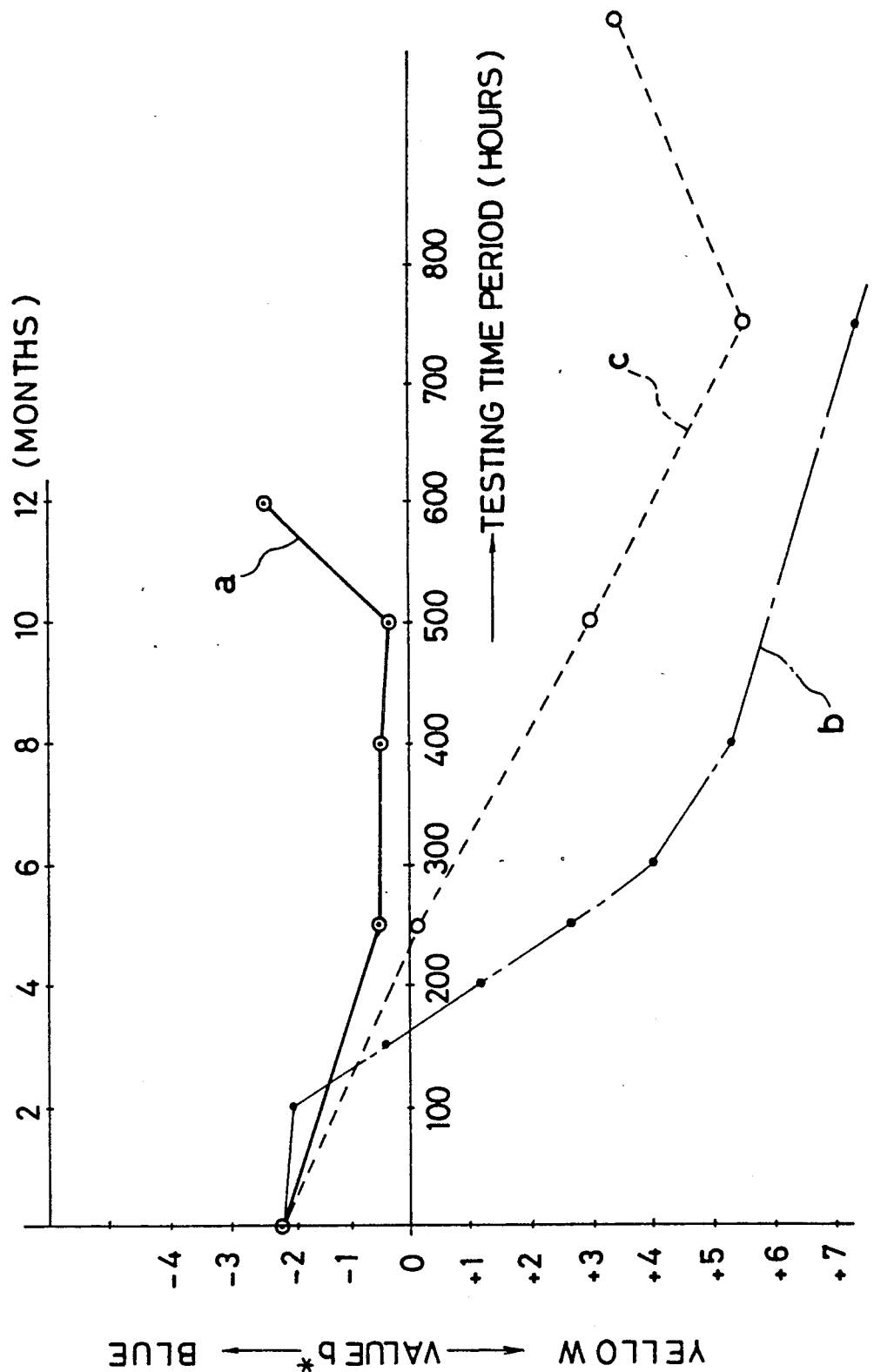
FIG. 8 is a graph which illustrates changes in value $b^*$ in the outdoor exposure test, and the tests according to the conventional examples 1 and 2.

Then the results of measurement of value L* are shown in FIGS. 7A, 7B, and 7C. Curve a shown in FIG. 7A illustrates change of value L* in the outdoor exposure test, wherein it gradually rises in accordance with time lapse, and value L* reaches 70 in 12 months. On the other hand, as designated by curves b and c shown in FIG. 7B, although value L* does not display a significant change in accordance with testing time lapse in the conventional examples 1 and 2, it is slightly lowered. As is shown, the completely different tendency from the results obtained in the outdoor exposure test is displayed.

On the other hand, as designated by curve d shown in FIG. 7C, value L* displays a gradual decrease tendency in the conventional example 3. Although value L* according to the present invention is temporarily lowered in accordance with time lapse as designated by curve e in this drawing, it again rises, and, as is shown, it reaches a deterioration state similar to the same after 12 months of the outdoor exposure in a significantly short time period of 50 hours. The referential example 2 displays, similarly to the conventional examples 1 and 2, a tendency in which no significant change is displayed.

Then, the results of measurement of value b* will be described. As designated by curve a shown in FIG. 8, value b* shows negative values (blue) at first. Then, it is temporarily changed to the value in the vicinity of zero, and it shows a tendency to greater negative values. On the other hand, as designated by curves b and c, value b* is changed to the positive values (yellow) in both the conventional examples 1 and 2. As is shown, a tendency in which the degree of color change to yellow on the surface of the sample is raised in accordance with time lapse.

Figure 9:
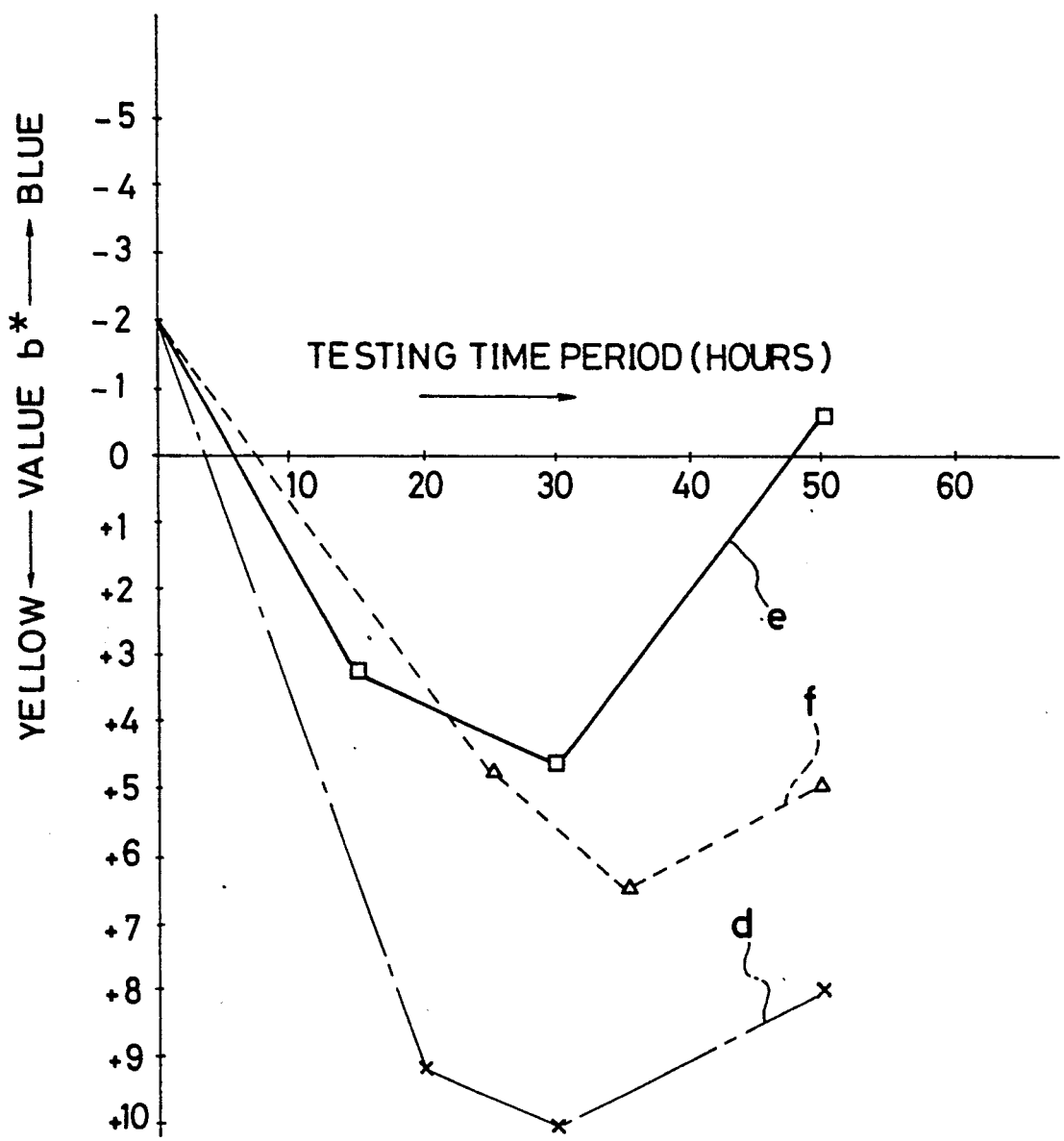
FIG. 9 is a graph which illustrates changes in value $b^*$ in the test according to the present invention, the tests according to the conventional example 3, and the referential example 2.

On the other hand, as designated by curve d shown in FIG. 9, value b* is changed to an extremely great positive value in a short time in accordance with the conventional example 3. Value b* obtained by the method according to the present invention is, as designate by curve d shown in this drawing, changed temporarily to positive values which display color change to yellow. However, it again returns to negative value after 50 hours has elapsed. As is shown, a similar tendency to that of the outdoor exposure is displayed. Referential example 2 shows a tendency, as designated by curve f of this drawing, in which value b* is changed, in a short time, to positive values, and then it comes closer to zero.

FIG. 10A is, as described above, a 200 times enlarged metallurgical microphotograph of the surface of the sample which has not been subjected to the test as yet. FIG. 10B is a 200 times enlarged metallurgical microphotograph of the surface of the sample which has been subjected to the weather resistance test according to the conventional example 3 for 50 hours. FIG. 10C is a 200 times enlarged metallurgical microphotograph of the surface of the sample which has been subjected to the weather resistance test according to the present invention. FIG. 10D is a 200 times enlarged metallurgical microphotograph of the surface of the sample after it has been subjected to the outdoor exposure test for 12 months. Although a spot pattern is formed on the surface of the sample according to the conventional example 3, such spot pattern is prevented on the surface of the sample according to the present invention. As is shown, a similar surface of the sample to that according to the outdoor exposure is obtained.

As can be clearly seen from data of results of each of the tests, when the weather resistance test is performed in accordance with the method of the present invention, a deterioration state which is extremely similar to that obtained by the outdoor exposure which takes a long time can be realized in a short time. Therefore, a fact that a satisfactorily correlative test results to the natural deterioration can be obtained is confirmed.

Although the material of the sample used in the tests in accordance with each of the above-described test methods comprises a hard vinyl chloride plate, substantially the same results were obtained by both the test method according to the present invention and the test method according to the conventional example 3 even if a soft vinyl chloride plate or a plate applied with acrylic paint is used as the sample. Consequently, the method of weather resistance test according to the present invention displays an advantage that generation of spot patterns and excessive color change on the surface of the sample can be prevented.

In the above-described embodiments, although a metal halide lamp with an irradiation wavelength of 300 to 450 nm and with an intensity of ultraviolet rays of 100±5 mW applied to the surface of the sample is used as the artificial light source, an artificial light source capable of radiating light including ultraviolet rays of the same intensity as that of the metal halide lamp and including visible radiation and/or infrared rays may be used. It is apparent that a similar effect can be obtained even if the above-described light source of the second type is used.

What is claimed is:

1. An apparatus for performing weather resistance test on a sample surface comprising:
   means for holding a sample having a surface to be tested;
   means including a source of ultraviolet light for applying ultraviolet rays to said sample surface;
   means including a source of moisture of condensing moisture on the surface of said sample;
   means for washing said surface of said sample with a cleaner; and
   means for controlling a repetitive cycle of operation of each of said means such that said ultraviolet light source is turned on for a first period of time after which the application of ultraviolet rays is terminated, whereafter said condensing means is operated for a second period of time after which the condensing is concluded, and said washing means is operated at least for a time between the time said condensing operation is concluded and said ultraviolet light source is turned on.

2. An apparatus for performing weather resistance tests according to claim 1, wherein said means for applying ultraviolet rays comprises a metal halide lamp radiating energy predominantly in a wavelength region from 300 to 450 nm and a filter for restricting said wavelength region to substantially 300 to 450 nm.

3. An apparatus for performing weather resistance tests according to claim 2, wherein said means for washing comprises spray nozzles disposed to spray said cleaner upon said sample surface.

4. An apparatus for performing weather resistance tests according to claim 2, wherein said means for holding said sample is inclined with respect to a horizontal plane.

5. An apparatus for performing weather resistance tests according to claim 4, wherein said means for washing comprises spray nozzles disposed to spray said cleaner upon said sample surface.

6. An apparatus for performing weather resistance tests according to claim 1, wherein said means for holding said sample is inclined with respect to a horizontal plane.

7. An apparatus for performing weather resistance tests according to claim 6, wherein said means for washing comprises spray nozzles disposed to spray said cleaner upon said sample surface.

8. An apparatus for performing weather resistance tests according to claim 1, wherein said means for washing comprises spray nozzles disposed to spray said cleaner upon said sample surface.

9. A method for performing a weather resistance test on a sample surface comprising the steps of:
   (a) exposing said sample surface to ultraviolet light radiation for a first period of time, after which said radiation exposure is terminated;
   (b) subjecting said sample to a process for condensing moisture on said surface for a second period of time, after which said condensing process is concluded; and
   (c) repeating alternately said ultraviolet light radiation exposure and said moisture condensing steps; wherein said method includes the further steps of
   (d) at least between said ultraviolet light radiation exposure step and said moisture condensing step, washing said surface to remove contaminants therefrom.

10. The method of claim 9, wherein said washing step is performed by spraying a cleaning solution from a spray nozzle onto said sample surface.

11. The method of claim 9, wherein said washing step is performed at the conclusion of said moisture condensing step before repetition of said ultraviolet light radiation exposure step.

12. The method of claim 11, wherein said washing step is performed by spraying a cleaning solution from a spray nozzle onto said sample surface.

13. The method of claims 11, wherein said washing step is also performed during said moisture condensing step.

14. The method of claim 13, wherein said washing step is performed by spraying a cleaning solution from a spray nozzle onto said sample surface.

15. The method of claim 11, wherein said washing step is also performed after termination of said ultraviolet light radiation exposure step before beginning said moisture condensing step.

16. The method of claim 15, wherein said washing step is performed by spraying a cleaning solution from a spray nozzle onto said sample surface.

17. The method of claim 15, wherein said washing step is also performed during said moisture condensing step.

18. The method of claim 17, wherein said washing step is performed by spraying a cleaning solution from a spray nozzle onto said sample surface.

* * * * *